(12) United States Patent
Hedgepeth et al.

(10) Patent No.: US 9,101,533 B2
(45) Date of Patent: Aug. 11, 2015

(54) NEEDLE SAFETY GUARD ADAPTED TO ATTACH TO A LIQUID CONTAINER

(71) Applicant: Mercy Medical Research Institute, Springfield, MO (US)

(72) Inventors: Bruce Hedgepeth, Ozark, MO (US); Roger Huckfeldt, Nixa, MO (US); Cindy Lowe, Nixa, MO (US); Martin Reuter, Flemington, MO (US); Matt Price, Springfield, MO (US); Keela Davis, Springfield, MO (US); Rahul Eapen, Monett, MO (US)

(*) Notice: Subject to any disclaimer, the term of this patent is extended or adjusted under 35 U.S.C. 154(b) by 273 days.

(21) Appl. No.: 13/889,106

(22) Filed: May 7, 2013

(65) Prior Publication Data

US 2013/0245593 A1    Sep. 19, 2013

Related U.S. Application Data

(63) Continuation of application No. 13/214,960, filed on Aug. 22, 2011, now Pat. No. 8,460,268.

(60) Provisional application No. 61/375,853, filed on Aug. 22, 2010.

(51) Int. Cl.
*A61J 1/20*    (2006.01)
*A61J 1/00*    (2006.01)
*B65D 43/00*   (2006.01)
*B65D 43/26*   (2006.01)
*A61J 1/14*    (2006.01)
*A61J 1/16*    (2006.01)
(Continued)

(52) U.S. Cl.
CPC *A61J 1/20* (2013.01); *A61J 1/1412* (2013.01); *A61J 1/1437* (2013.01); *A61J 1/16* (2013.01); *A61J 2001/1425* (2013.01); *A61M 5/1782* (2013.01); *A61M 5/3213* (2013.01)

(58) Field of Classification Search
CPC ............. Y10S 215/00; A61J 1/00; A61J 1/20; D65D 39/00; B65D 45/00; B65D 43/00; B65D 43/26
USPC ......................................... 604/415; 215/230
See application file for complete search history.

(56) References Cited

U.S. PATENT DOCUMENTS 3,552,591 A    1/1971    Wimmer
4,840,618 A    6/1989    Marvel
(Continued)

OTHER PUBLICATIONS

U.S. Appl. No. 13/889,127 Office Action dated Dec. 19, 2014, 14 pages.

*Primary Examiner* — Tatyana Zalukaeva
*Assistant Examiner* — Sara Sass
(74) *Attorney, Agent, or Firm* — Michael A. Williamson; Polsinelli PC

(57) ABSTRACT

A needle safety guard device adapted to attach to a liquid container is provided. The device includes a disk-shaped shield having a medial opening connected with a radial opening between two radial edges. The device also includes a substantially U-shaped holder having two sidewalls coupled substantially perpendicular to the disk-shaped shield along the two radial edges, and a top cover connecting to the two sidewalls and extending from the shield above the radial opening. The U-shaped holder includes a wedged protrusion and a curved protrusion extending from each of the two sidewalls, the curved protrusion being between the top cover and the wedged protrusion for blocking a cap of the liquid container from moving toward the medial opening.

11 Claims, 18 Drawing Sheets

(51) Int. Cl.
*A61M 5/178* (2006.01)
*A61M 5/32* (2006.01)

(56) References Cited

U.S. PATENT DOCUMENTS

| | | | |
|---|---|---|---|
| 4,944,736 A | 7/1990 | Holtz | |
| 4,982,850 A | 1/1991 | Mears | |
| 5,301,850 A * | 4/1994 | Gueret | 222/494 |
| 5,356,406 A | 10/1994 | Schraga | |
| 5,624,404 A | 4/1997 | Fisler | |
| 5,788,099 A * | 8/1998 | Treu et al. | 215/230 |
| 5,951,524 A | 9/1999 | Enriquez | |
| 5,954,104 A | 9/1999 | Daubert et al. | |
| 6,364,866 B1 | 4/2002 | Furr et al. | |
| 6,453,956 B2 | 9/2002 | Safabash | |
| 2002/0019622 A1 | 2/2002 | Daubert et al. | |
| 2004/0059269 A1 | 3/2004 | Ballard et al. | |
| 2006/0108319 A1 | 5/2006 | Meittunen | |
| 2009/0299325 A1 | 12/2009 | Vedrine et al. | |
| 2012/0065611 A1 | 3/2012 | Musani | |

* cited by examiner

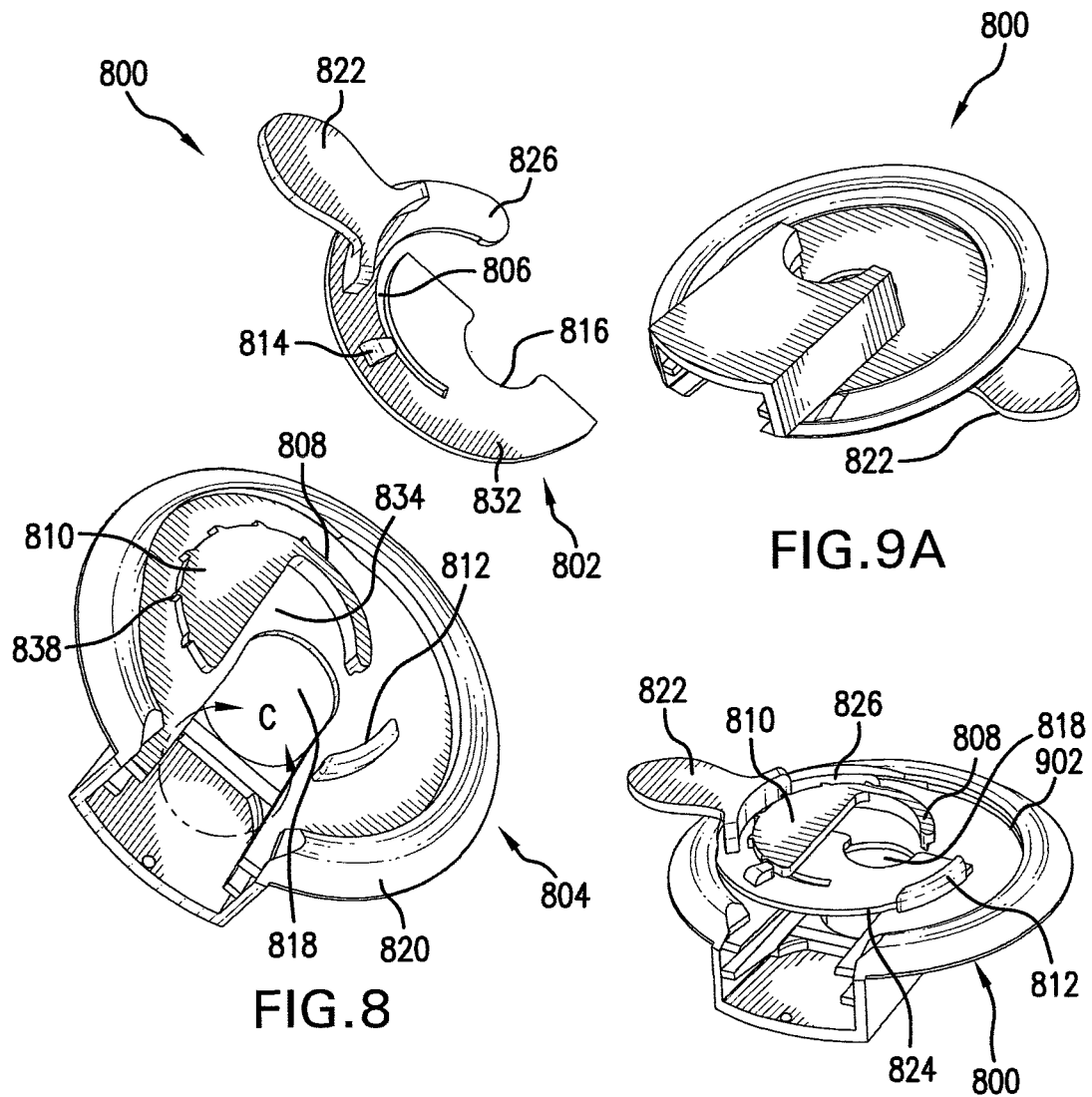
FIG.9A
FIG.8
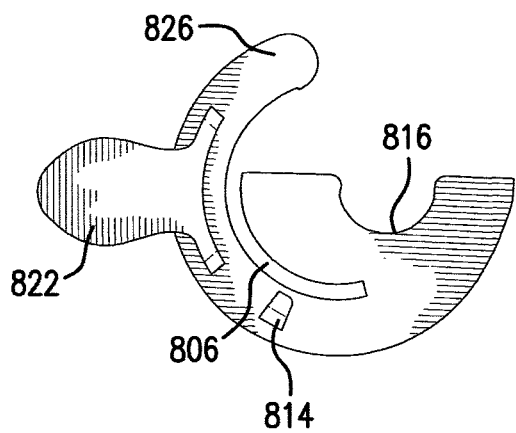
FIG.9C
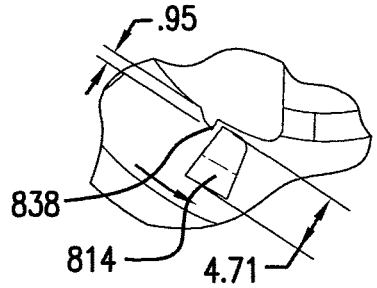
FIG.9B
FIG.9D

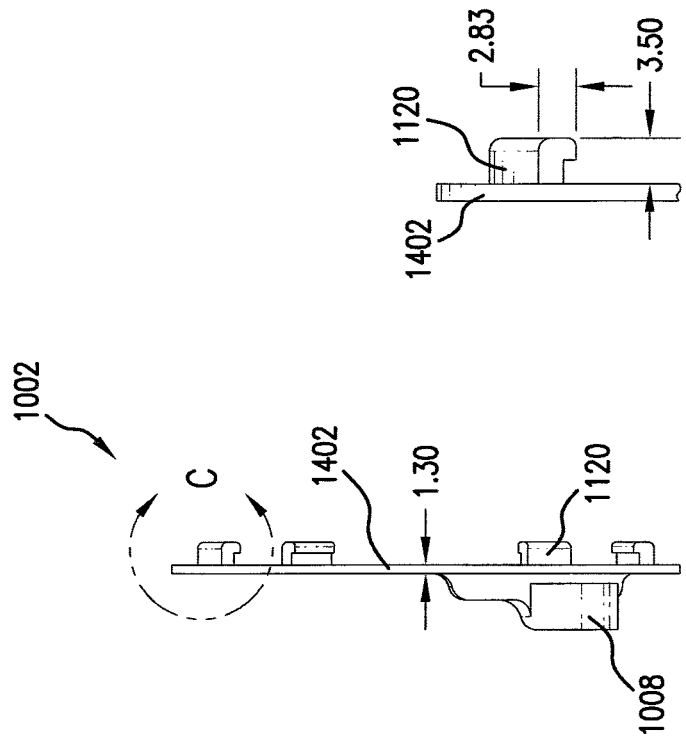
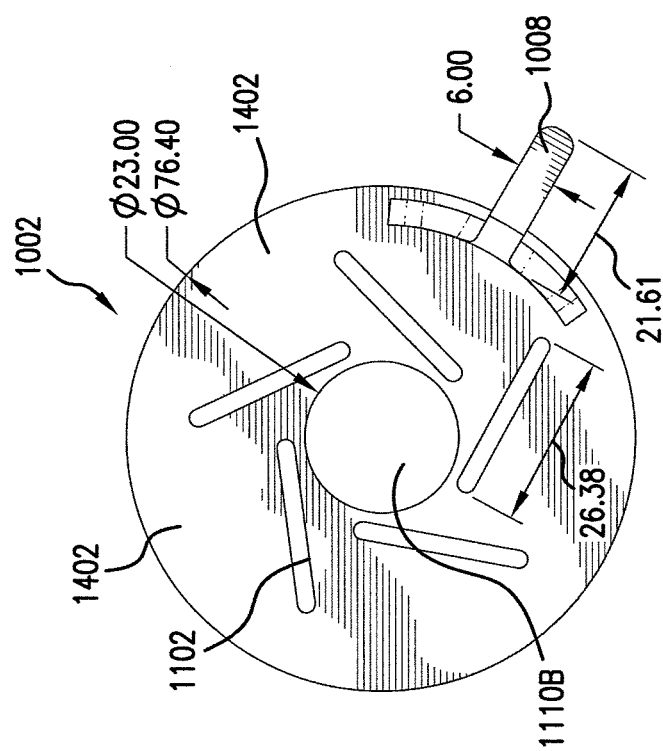

NEEDLE SAFETY GUARD ADAPTED TO ATTACH TO A LIQUID CONTAINER

RELATED APPLICATIONS

This application is a continuation of U.S. patent application Ser. No. 13/214,960, filed on Aug. 22, 2011, which claimed priority to U.S. Patent Application No. 61/375,853, filed on Aug. 22, 2010, both of which are incorporated by reference herein.

BACKGROUND OF THE INVENTION

This invention relates to a device that attaches to a liquid container, de-caps the container and prevents medical personnel from being injured by a syringe used to draw liquid from the container.

During procedures, it is often necessary for a healthcare provider to inject medications into a patient. It is not desirable for the healthcare provider to remove his or her gloves and touch a vial or a liquid container that contains medications or medical solutions. A nurse or a medical assistant may hold the vial while the healthcare provider sticks a needle laden syringe into the vial to withdraw the medications from the vial. Accidents sometimes occur whereby the healthcare provider inadvertently injures the nurse or medical assistant's hand with a sharp needle of the syringe. Furthermore, a vial that contains medications or other liquid material normally has a pierce-able cover, which is protected with a vial cap. When a healthcare provider removes the vial cap with gloves on, the pierce-able cover may be contaminated.

Therefore, it is desirable to develop a safety device for protecting medical personnel from needle sticks.

BRIEF SUMMARY

This disclosure advances the art and overcomes the problems outlined above by providing a safety guard adapted to attach to a vial for protecting medical personnel holding a vial from injury when a healthcare provider withdraws medication from the vial with a needle laden syringe. The safety guard also minimizes contamination of the pierce-able cover of the vial during removal of the vial cap that covers the pierce-able cover.

In one embodiment, a needle safety guard device adapted to attach to a liquid container is provided. The device includes a disk-shaped shield having a medial opening connected with a radial opening between two radial edges. The device also includes a substantially U-shaped holder having two sidewalls coupled substantially perpendicular to the disk-shaped shield along the two radial edges, and a top cover connecting to the two sidewalls and extending from the shield above the radial opening. The U-shaped holder includes a wedged protrusion and a curved protrusion extending from each of the two sidewalls, the curved protrusion being between the top cover and the wedged protrusion for blocking a cap of the liquid container from moving toward the medial opening.

According to embodiments of the present disclosure, the wedged protrusion has a tapered portion near an outer edge of the shield such that the tapered portion generates enough upward wedging force to remove the cap. The disk-shaped shield includes a recessed bottom portion below an outer circumferential edge of the disk-shaped shield and an inner circumferential edge around the medial opening. The two radial edges are separated by a distance gradually decreasing toward the medial opening such that the liquid retainer is retained within the medial opening. The two sidewalls and the wedged protrusion and the curved protrusion are substantially symmetric to the top cover. The shield and raised U-shaped holder include a plastic.

In a particular embodiment, a needle safety guard device adapted to attach to a liquid container is provided. The device includes a disk-shaped shield having a medial opening connected with a radial opening between two radial edges. The device also includes a substantially U-shaped holder having two sidewalls coupled substantially perpendicular to the disk-shaped shield along the two radial edges, and a top cover connecting to the two sidewalls and extending from the shield above the radial opening. The U-shaped holder includes a wedged protrusion and a curved protrusion extending from each of the two sidewalls, the curved protrusion being between the top cover and the wedged protrusion for blocking a cap of the liquid container from moving toward the medial opening. The wedged protrusion has a tapered portion near an outer edge of the shield such that the tapered portion generates enough upward wedging force to remove the cap. The disk-shaped shield includes a recessed bottom portion below an outer circumferential edge of the disk-shaped shield and an inner circumferential edge around the medial opening. The two radial edges are separated by a distance gradually decreasing toward the medial opening such that the liquid retainer is retained within the medial opening. The two sidewalls and the wedged protrusion and the curved protrusion are substantially symmetric to the top cover. The shield and raised U-shaped holder include a plastic.

In another embodiment, a needle safety guard device adapted to attach to a liquid container is provided. The device includes a shield base having a medial opening connected with a radial opening. The device also includes a ratchet component coupled to a bottom of the shield base. The device further includes a rotary slider coupled to the ratchet component with a plurality of teeth. The slider has a neck portion being movable for fitting to the liquid container. The device also includes a pawl attached to the bottom of the shield base to engage with one of the plurality of teeth of the ratchet component. The device also includes a rail component attached to the bottom of the shield base for retaining the rotary slider. The device further includes a substantially U-shaped holder coupled to a top of the shield base above the radial opening.

According to embodiments of the disclosure, the neck portion of the rotary slider is substantially concave shaped such that the liquid container partially contacts the neck portion of the rotary slider and partially contacts the medial opening of the shield base and is retained within the shield base. The position of the neck portion of the rotary slider relative to the medial opening is adjustable by manually moving a handle coupled to the rotary slider. The U-shaped holder includes two sidewalls coupled substantially perpendicular to the shield base along two radial edges of the radial opening, and a top cover connecting to the two sidewalls and extending from the shield base above the radial opening. The U-shaped holder includes a wedged protrusion and a curved protrusion extending from each of the two sidewalls. The curved protrusion is between the top cover and the wedged protrusion for blocking a cap of the liquid container from moving toward the medial opening. The wedged protrusion has a tapered portion near an outer edge of the shield such that the tapered portion generates enough upward wedging force to remove the cap. The two sidewalls and the wedged protrusion and the curved protrusion are substantial The shield base includes a recessed bottom portion below an outer circumferential edge of the disk-shaped shield and an inner circumferential edge around the medial opening. The shield base is substantially disk-shaped. Two radial edges of the radial opening are separated by a distance gradually decreasing toward the medial opening such that the liquid retainer is retained within the medial opening. The shield and raised U-shaped holder include a plastic.

In a further embodiment, a needle safety guard device adapted to attach to a liquid container is provided. The device includes a top shield having a central opening, and a plurality of through-holes spaced along a first circle between the central opening and an outer edge of the top shield. The device also includes a plurality of snap clip guides extending from a bottom of the top shield and being positioned along a second circle between the outer edge and the first circle. The device further includes a shield base having a plurality of sliding slots and a plurality of snap clips attached on a top of the shield base, where the snap clips are configured to attach to the snap clip guides and to be movable along the respective snap clip guides. The device also includes an Iris capture component coupled to a bottom of the top shield near the central opening for adjusting to fit to the liquid container, the Iris capture component including a plurality of Iris blades coupled to the top shield and the plurality of sliding slots of the shield base. The device also includes a handle attached to the bottom of the shield base for manually moving the blades within the respective sliding slots to adjust the Iris capture component to fit to the liquid container.

According to embodiments of the disclosure, each of the Iris blade includes a protrusion on a bottom side of the Iris blade, the protrusion being coupled to each respective sliding slot. The device also includes a plurality of blade tabs, each of the Iris blade having a hole on a top side of the Iris blade for attaching the Iris blades to the top shield with the plurality of blade tabs, and the hole being aligned with the respective through-hole in the top shield and sized for press fits with the blade tabs. The shield base includes a plurality of teeth along an outer edge of the shield base. The handle includes a locking component engaged with the plurality of teeth for locking the position of the blades. The top shield includes a recessed portion between an outer edge and the medial opening. The device includes a plastic. The top shield and the shield base are substantially disk-shaped.

In still yet another embodiment, a method is provided for decapping a vial with a safety shield with a substantially U-shaped holder extending upward from a shield base. The method includes placing the vial with a vial cap on a pair of wedged protrusions extending from two opposing sidewalls of the U-shaped holder, where the two opposing sidewalls are separated by a top wall of the U-shaped holder. The method also includes sliding the vial along the wedged protrusion toward a central opening and forcing the vial against a pair of curved protrusions extending from the two sidewalls between the top wall and the wedged protrusions. The method further includes retaining the vial cap within the substantially U-shaped holder and the vial within the central opening.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings.

BRIEF DESCRIPTION OF THE DRAWINGS

FIG. 8 is a perspective view of an adjustable safety guard with rotary slider for adjustable vial size prior to assembly in an embodiment.

FIG. 9A is a perspective top view of the assembled adjustable safety guard of FIG. 8.

FIG. 9B is a perspective bottom view of the assembled adjustable safety guard of FIG. 8.

FIG. 9C is a top view of the slider of FIG. 8.

FIG. 9D is an enlarged view of the ratchet-pawl mechanism with exemplary dimensions of FIG. 8.

FIG. 14A is a bottom view of the lower disk of the safety shield of FIG. 11.

FIG. 14B is a side view of the lower disk of the safety shield of FIG. 11.

FIG. 14C is a side view of the lower disk snap clip of the safety shield of FIG. 11.

DETAILED DESCRIPTION

Figure 1A:
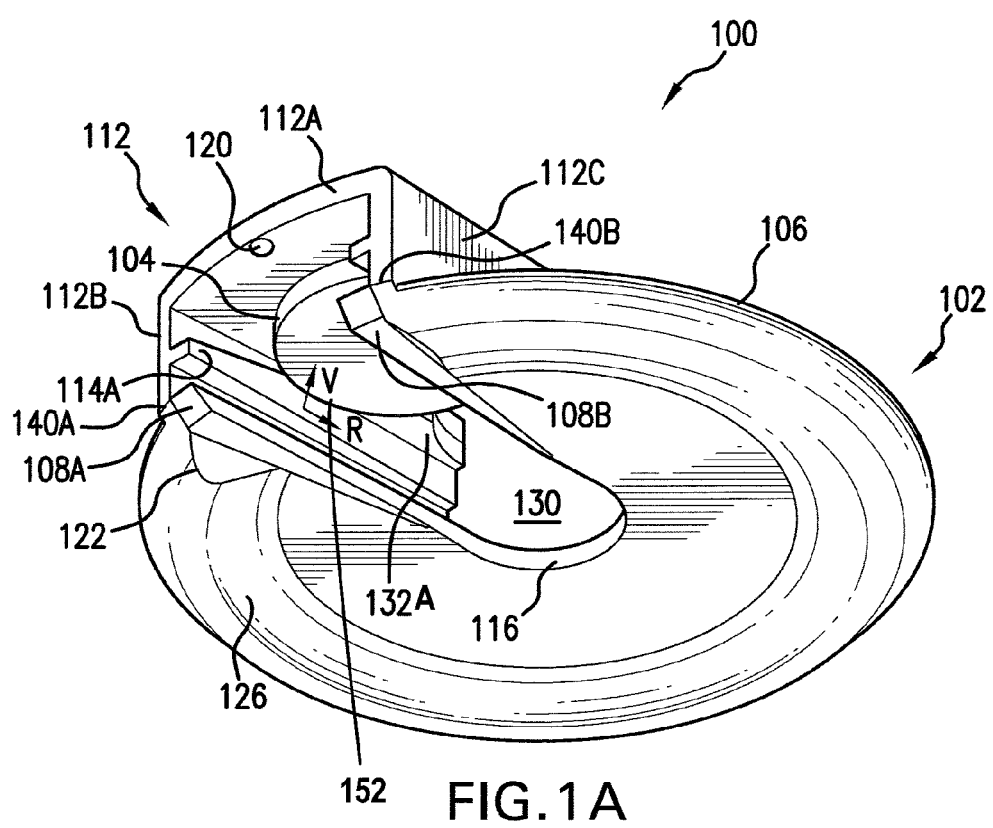
FIG. 1A is a perspective bottom view of the safety guard in an embodiment.

The present disclosure may be understood by reference to the following detailed description taken in conjunction with the drawings as briefly described below. It is noted that, for purposes of illustrative clarity, certain elements in the drawings may not be drawn to scale.

FIG. 1A is a perspective view of a safety guard from the bottom and outside in an embodiment. Safety guard 100 is adapted to attach to a vial (see FIG. 2 for a simplified diagram). Safety guard 100 includes a disk-shaped shield 102 and a substantially U-shaped holder 112. Disk-shaped shield 102 serves as a guard to protect a medical assistant from being injured by a needle as a physician or other user inserts the needle into the vial to withdraw liquid. U-shaped holder 112 attached to disk-shaped shield 102, removes a vial cap 104 from the vial, and retains the vial cap removed from the vial.

Disk-shaped shield 102 has an outer circumferential edge 106, an inner circumferential edge 116, and a middle portion 126 therebetween. Middle portion 126 is recessed from outer circumferential edge 106 and inner circumferential edge 116. Recessed middle portion 126 may be curved as illustrated by curved edge 122. The recessed middle portion with outer circumferential edge 106 raised from recessed middle portion 126 will stop a needle that may accidentally strike the shield when a physician uses the syringe to withdraw medications from a vial.

Disk-shaped shield 102 includes a substantially medial opening 130 surrounded by inner edge 116 and a radial opening connected to the medial opening 130. The radial opening is bounded by two radial edges 108A-B (Item 108B not shown in FIG. 1A). Radial edges 108A-B are straight and flat. A vial can be pushed through the radial opening toward the medial opening 130 of disk-shaped shield 102. The vial is retained within the medial opening that is smaller than the sealed cover 204 of the vial, but larger than the vial neck 206 (see FIG. 2). Radial edges 108A-B help guide the vial through the radial opening.

U-shaped holder 112 includes a top portion 112A connected to two sidewalls 112B-C. Sidewalls 112B-C are attached perpendicularly to disk-shaped shield 102 such that top portion 112A is raised above the radial opening of disk-shaped shield 102. The attachments 140A-B are along two radial edges 108A-B, but at a distance from the two radial edges.

U-shaped holder 112 also includes wedged protrusions 114A-B extending from respective sidewalls 112B-C configured for removing and retaining vial cap 104. The wedged protrusions have dimensional variations in both radial direction and vertical direction as shown by arrows R and V, respectively. Details of wedged protrusions are further illustrated in FIGS. 3A-3B.

U-shaped holder 112 also includes curved protrusions 132A and 132B (not shown) extending from respective sidewalls 112B-C, for blocking vial cap 104 from moving toward the medial opening 130 of disk-shaped shield 102. Curved protrusions 132A-B are positioned above wedged protrusions 114A-B closer to top portion 112A. The curvatures of curved protrusions 132A-B match to the circumference of vial cap 104, such that when a vial is forced through the radial opening toward the medial opening 130 of disk-shaped shield 102, vial cap 104 is blocked by the curved protrusions 132A-B. As the vial is manually forced to move toward the medial opening 130 by a personnel holding a vial, vial cap 104 is removed from the vial without touching the vial cap 104 by the medical personnel (see FIG. 3B and related detailed description on the mechanism for removing the cap). Vial cap 104 is then retained on the top of wedged protrusions 114A-B.

U-shaped holder 112 also includes a locking mechanism or bump 120 near the outer edge of top portion 112A for locking vial cap 104 inside U-shaped holder 112, such that vial cap 104 does not fall from the disk-shaped shield 102.

Figure 1B:
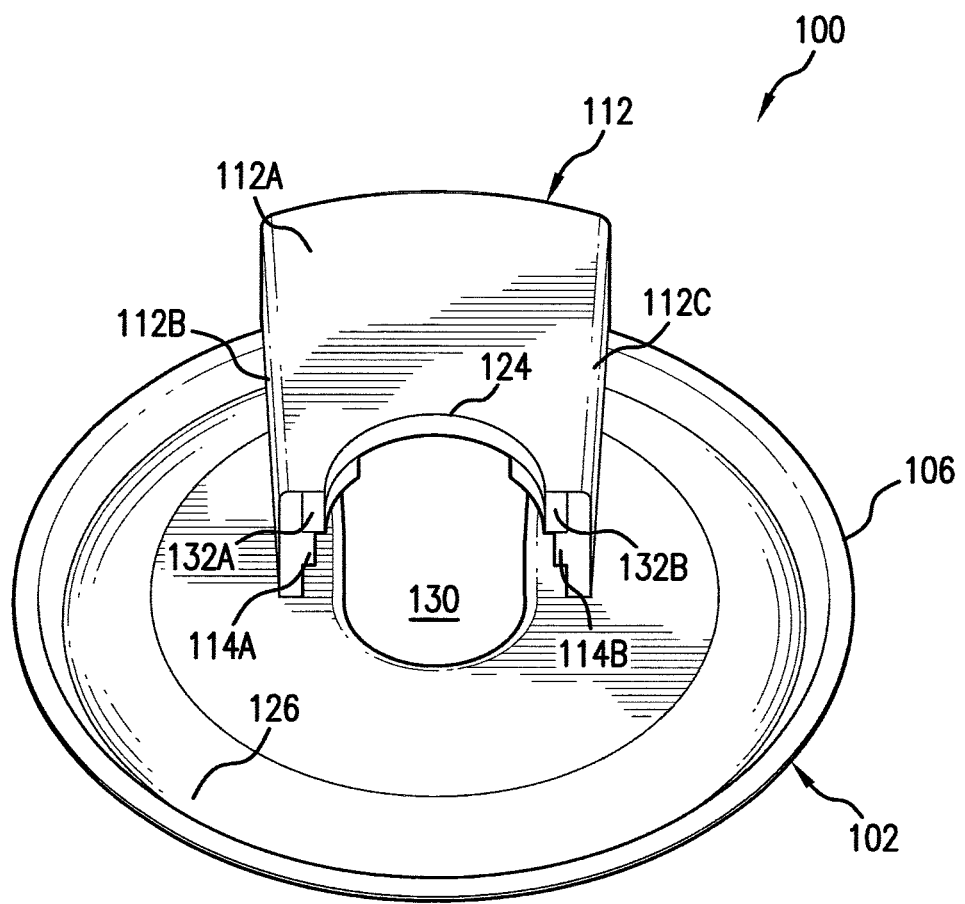
FIG. 1B is a top, center perspective view of the safety guard of FIG. 1A in an embodiment.

FIG. 1B is a perspective view of the safety guard 100 of FIG. 1A from the top and center in an embodiment. FIG. 1B shows a raised circumferential outer edge 106, a recessed middle portion 126 for disk-shaped shield 102. FIG. 1B also illustrates that U-shaped holder 112 is raised above disk-shaped shield 102 by sidewalls 112B-C. As shown, top portion 112A of U-shaped holder 112 has a curved edge 124 near the medial opening 130 of disk-shaped shield 102. The curved edge 124 is substantially circular and is sized to expose the pierce-able cover 208 of vial 202 (see FIG. 2). Curved protrusion 132A and wedged protrusion 114A are viewed from the center.

Figure 2:
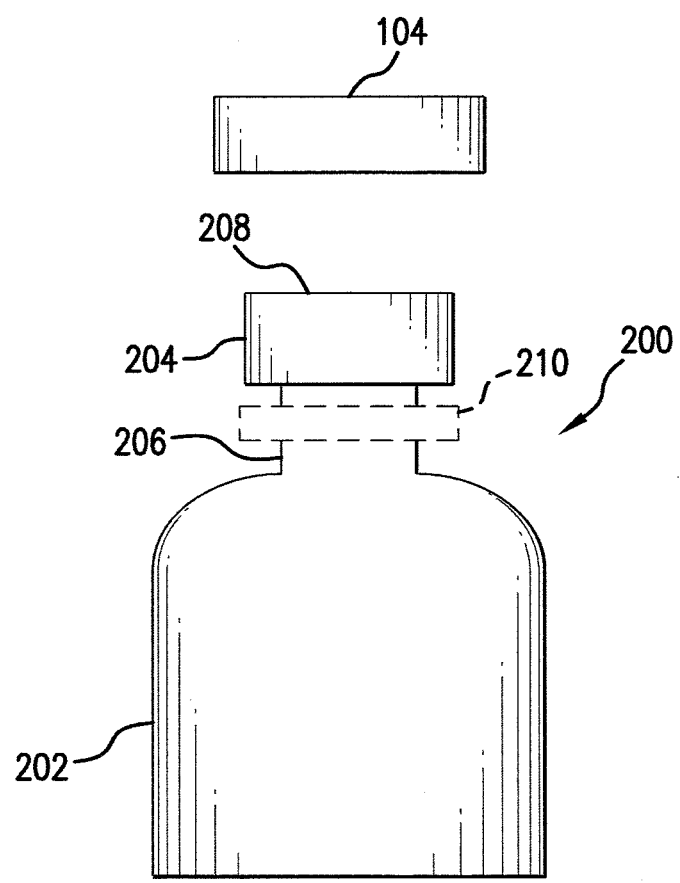
FIG. 2 is a simplified diagram of a vial or a liquid container in an embodiment.

FIG. 2 illustrates a simplified diagram of a vial in an embodiment. Vial 200 includes a liquid container 202 and a sealed cover 204 connected to container 202 by a vial neck portion 206. Neck portion 206 has a smaller diameter than sealed cover 204. Sealed cover 204 has a center opening to expose a pierce-able cover 208 manufactured from rubber, vinyl, silicone or similar materials known in the industry (also see a photo of a safety guard in FIG. 7). Sealed cover 204 may be made of a metal, such as aluminum. Vial cap 104 covers and protects the pierce-able cover 208 and the sealed cover 204 is removable from vial 200. Generally, vial caps 104 are removably fastened to the seal 206 and are easily removed with moderate upward force.

Vial 200 may optionally have an annual ring 210 around the neck portion 206. Space between sealed cover 204 and ring 210 must be larger than the thickness of radial edges 108A-B.

Figure 3A:
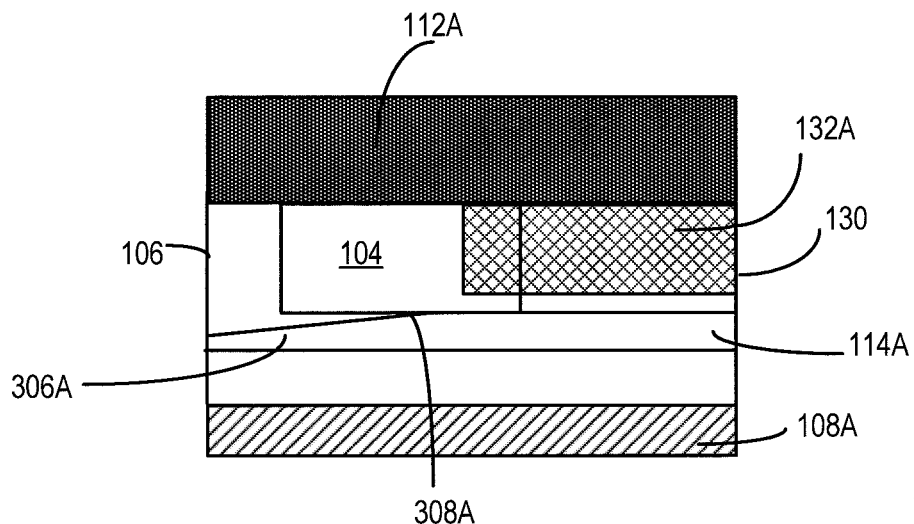
FIG. 3A is a simplified cross-sectional view of sidewall of U-shaped holder in an embodiment.

FIG. 3A is a simplified cross-sectional view of the sidewall of U-shaped holder in an embodiment. As illustrated, sidewall 112B of U-shaped holder is connected to top portion 112A of U-shaped holder 112. Curved protrusion 132A is positioned near the medial opening 130 of disk-shaped shield 102 and, is located above wedged protrusion 114A, close to top portion 112A. Wedged protrusion 114A tapers to become thinner near the outer edge 106 of disk-shaped shield 102 than near the medial opening 130 of disk-shaped shield 102. The tapered portion 306A allows the vial cap 104 to move toward the medial medial opening 130 without decapping near outer edge 106 of safety guard 100, and provides an upward force and assists vial cap 104 removal from sealed cover 206. Note that the tapered portion 306A ends at point 308A. Radial edge 108A is below wedged protrusion 114A for guiding the vial through the radial opening toward medial opening 130.

Figure 3B:
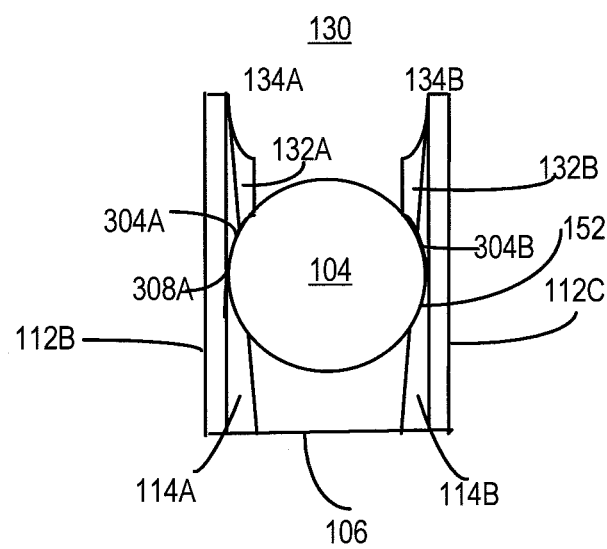
FIG. 3B is a simplified top view of curved protrusion and wedged protrusion from sidewall in an embodiment.

FIG. 3B is a simplified top view of curved protrusion and wedged protrusion from the sidewall in an embodiment. As illustrated, two curved protrusions 132A and 132B extend from respective sidewalls 112B and 112C. Curved protrusions 132A and 132B have outer curved sides 134A and 134B toward the medial opening 130 of disk-shaped shield 102 for exposing the pierce-able cover 208 of vial 200. Curved protrusions 132A and 132B also have inner curved sides 304A and 304B for fitting to vial cap 104 to block movement of vial cap 104 toward the medial opening 130.

Wedged protrusions 114A and 114B have reduced dimensions from outer edge 106 of disk-shaped shield 102 toward the medial opening 130 of disk-shaped shield 102, such that vial neck 204 contacts wedged protrusions 114A-B near outer edge 106. Wedged protrusions 114A-B also have clearance from protrusion 114A-B toward the medial opening 130. Sizes of wedged protrusions 114A-B are determined such that upward wedging force is generated between sealed cover 204 and wedged protrusions 114A-B near outer edge 106. The upward wedging force is high enough to remove vial cap 104. After removable of vial cap 104, wedging force is reduced when the vial cap 104 moves away from the outer edge 106 of disk-shaped shield 102. As illustrated in FIG. 3B, wedged protrusion 114A is tapered toward outer edge 106 such that the vial is retained within the medial opening 130, and curved protrusion 132A extends more than wedged protrusion 114A from sidewall 112B for blocking the cap 104 from moving toward the medial opening 130.

As illustrated in FIG. 3B, vial cap 104 is pressed against inner sides 304A and 304B of curved protrusions 132A and 132B, and a portion of vial cap 104 bridges on wedged protrusions 114A-114B. Note that end 308A of the tapered portion is near inner side 304A of curved protrusion 132A. This configuration allows removal of vial cap 104 without touching the vial cap 104 by a user. For example, a medical personnel holding a vial may push the vial toward the medial opening 130. Vial cap 104 is then engaged with the inner sides 304A and 304B of the curved protrusions 132A and 132B, and blocked by the curved protrusions from moving toward the medial opening 130. The lower edge 152 of the vial cap 104 bridges across the upper edges 302A and 302B of the wedged protrusions 134A-134B.

Figure 4A:
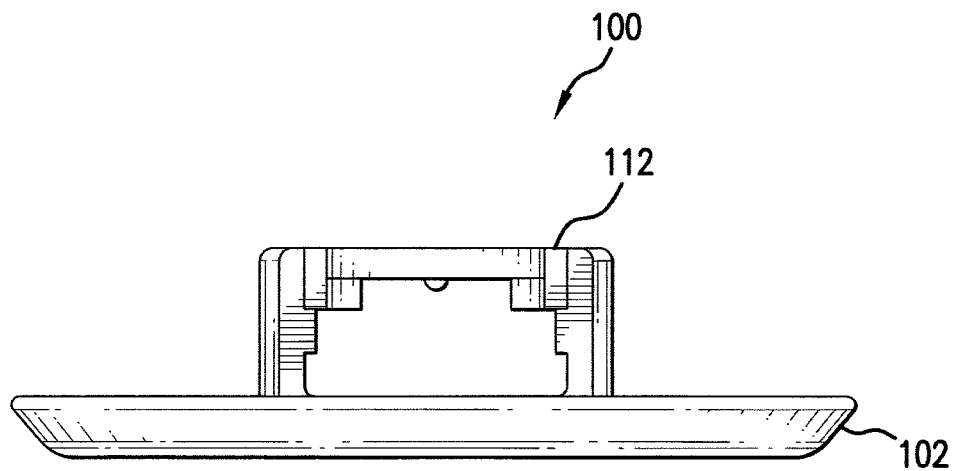
FIGS. 4A-4C are side views of the safety guard of FIG. 1A in an embodiment.
Figure 4B:
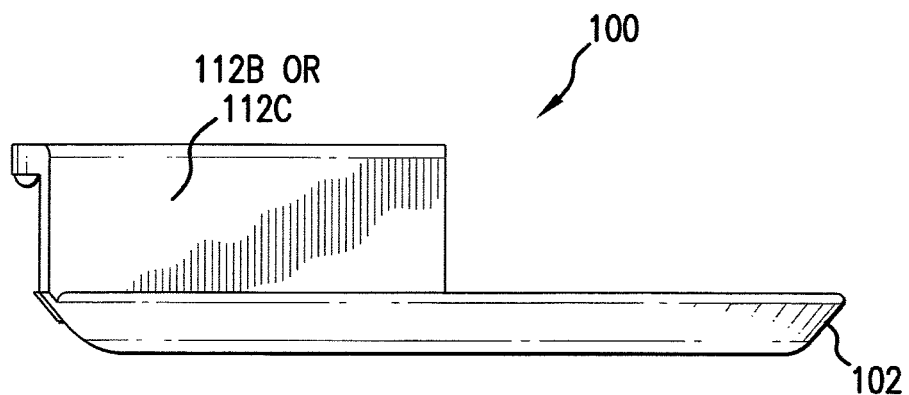
Figure 4C:
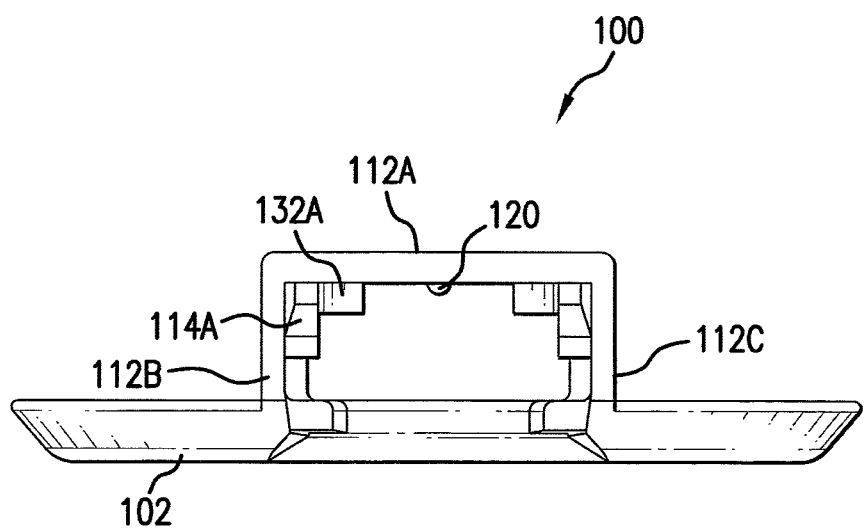

FIGS. 4A-4C are different side views of safety guard 100 that is adapted to attach to a vial in an embodiment. FIG. 4A is a side view from the opposite side facing the U-shaped holder. FIG. 4B shows that U-shaped holder 112 is raised from disk-shaped shield 102. FIG. 4C is a front view facing the U-shaped holder.

Figure 5:
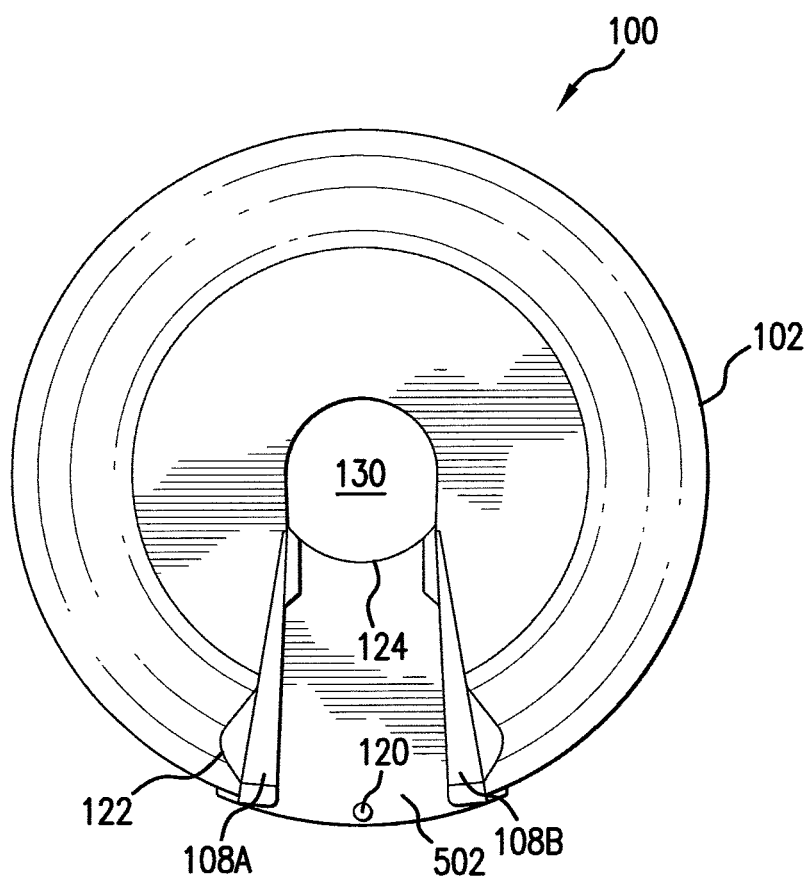
FIG. 5 is a bottom view of the safety guard of FIG. 1A in an embodiment.

FIG. 5 is a bottom view of safety guard 100 in an embodiment. As illustrated in FIG. 5, radial edges 108A-B are straight to allow the sealed cover 204 of vial 200 to slide toward the medial opening 130 of the disk-shaped shield 102. Raised edges 108A-B become closer toward the medial opening 130 such that radial opening 502 becomes narrow toward the medial opening 130, which helps the vial 200 retain within the medial opening 130. Radial opening 502 between radial edges 108A-B is sized large enough to allow neck portion 206 of vial 200 to pass through with clearance, but small enough to retain the vial 200. Vial 200 may be made of glass or plastic or any other material.

As illustrated in FIG. 5, locking mechanism or bump 120 is positioned near outer edge 106 of disk-shaped shield 102. FIG. 5 also shows that radial edges 108A-B are wedge-shaped. Curved protrusions 132A-B extend beyond radial edges 108A-B. FIG. 5 further shows that top portion 112A has a curved edge 124 toward medial opening 130. Bottom portion of disk-shaped shield 102 is curved as illustrated by curvature 122.

Safety guard 100 is designed for easy use. A vial is manipulated into the safety guard by aligning the vial neck portion 206 with the opening. The sealed cap 204 is positioned between sidewalls 112B-C above raised edges 108A-B. As the vial 200 is forced toward medial opening 130, the vial cap 104 is forced onto wedged protusions 114A-B and blocked by curved protrusions 132A-B, and is removed by the upward wedge force. The vial cap can be removed with the safety guard and retained in the vial cap holder. More specifically, a neck portion of the vial can be pushed through the radial opening toward the medial opening 130 of disk-shaped shield 102. By pushing through the radial opening of disk-shaped shield 102, vial cap 104 is removed and retained on wedged edges 114A-B and secured by curved protrusions 132A-B and locking mechanism 120 in the U-shaped holder.

Figure 6A:
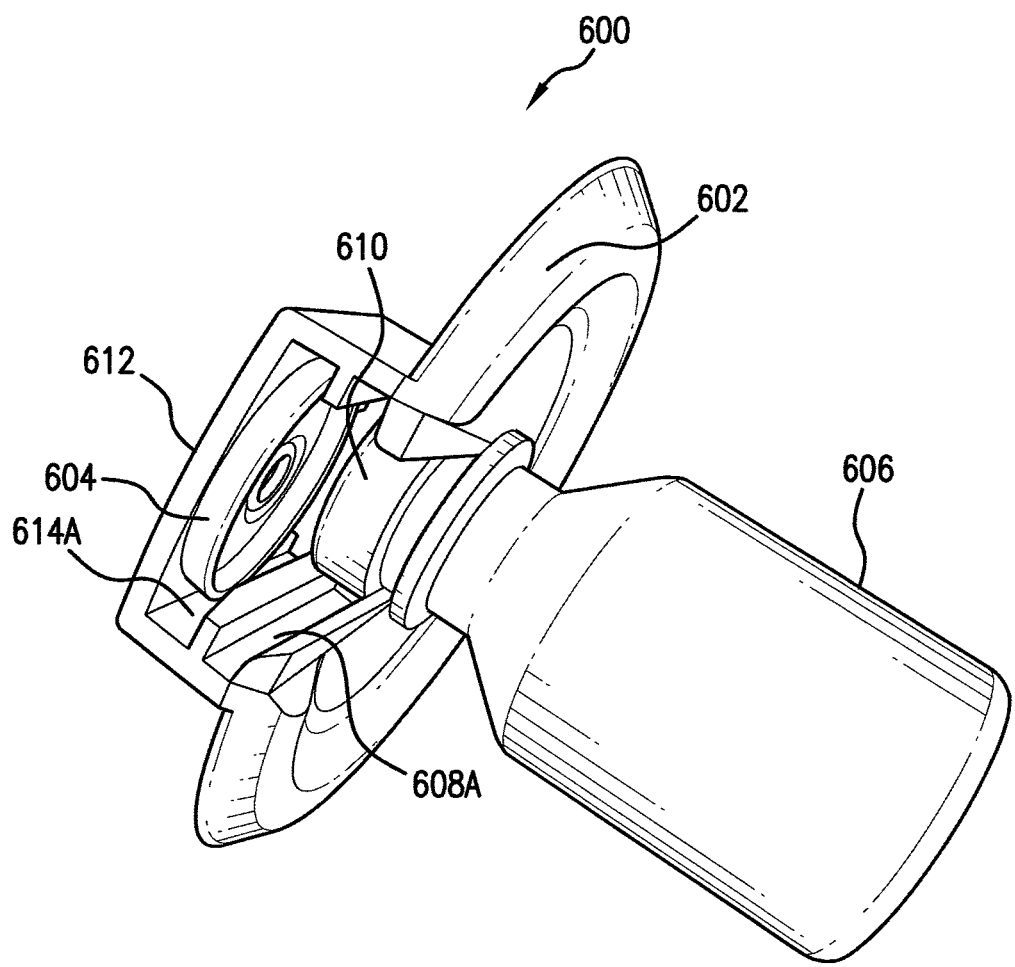
FIG. 6A is a perspective view of a safety guard in use on a vial in an embodiment.

FIG. 6A is a perspective view of safety guard 100 that is attached to a vial of medication or other liquid material in an embodiment. Safety guard 600 includes a disk-shaped shield 602 and a U-shaped holder 612 that has a top portion and two sidewalls that attach to disk-shaped shield 602. Between radial edges 608A-B is an open space for vial 606 to pass through. Vial 606 is frictionally engaged to wedged edge 614A-B of U-shaped holder 612. Vial cap 604 is removed from sealed cover portion 610 of vial 606 by the frictional force between sealed cover portion 610 and wedged edges 614A-B and is held in the U-shaped holder 612. FIG. 6A also shows wedged protrusions 614A-B extending from sidewalls 612B-C for holding vial cap 604.

Figure 6B:
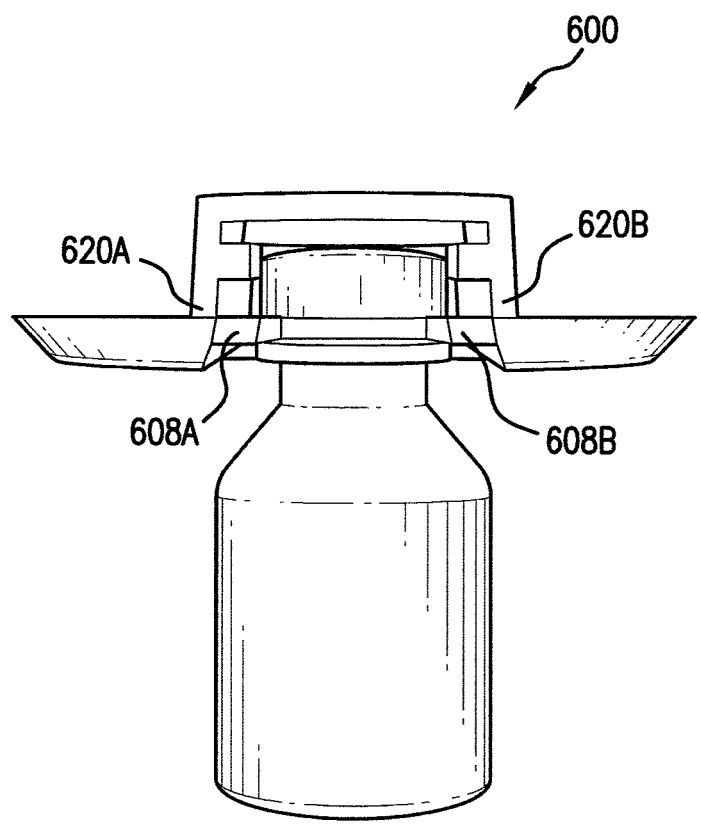
FIG. 6B is a side view of a safety guard in use on a vial in an embodiment.

FIG. 6B is a front view of the safety guard of FIG. 6A. It is referenced to a pen to illustrate a size of the safety guard. Radial edges 608A-B are flat to allow neck portion 610 of vial 606 to slide inward toward the medial opening of the disk-shaped shield 602. Attachments 620A-B for sidewalls to shield are along two radial edges 608A-B, but at a distance from radial edges.

Vials may vary in sizes or volumes, generally ranging from 5 ml to 250 ml. In a particular embodiment, a vial of 30 ml may have vial cap of about 20 mm diameter, a bottom diameter of 30 mm and a height of about 65 mm. The disk-shaped shield 602 may be 75 mm in diameter. U-shaped Holder 612 may be raised from disk-shaped shield 602 for about 10 mm, 30 mm across the radial opening and a radial length of about 35 mm. Vial cap 604 may have a diameter of about 23 mm slightly larger than the vial cover 610. It will be appreciated by those of skilled in the art that safety guard 100 may vary in dimensions, shapes or geometries.

Figure 7:
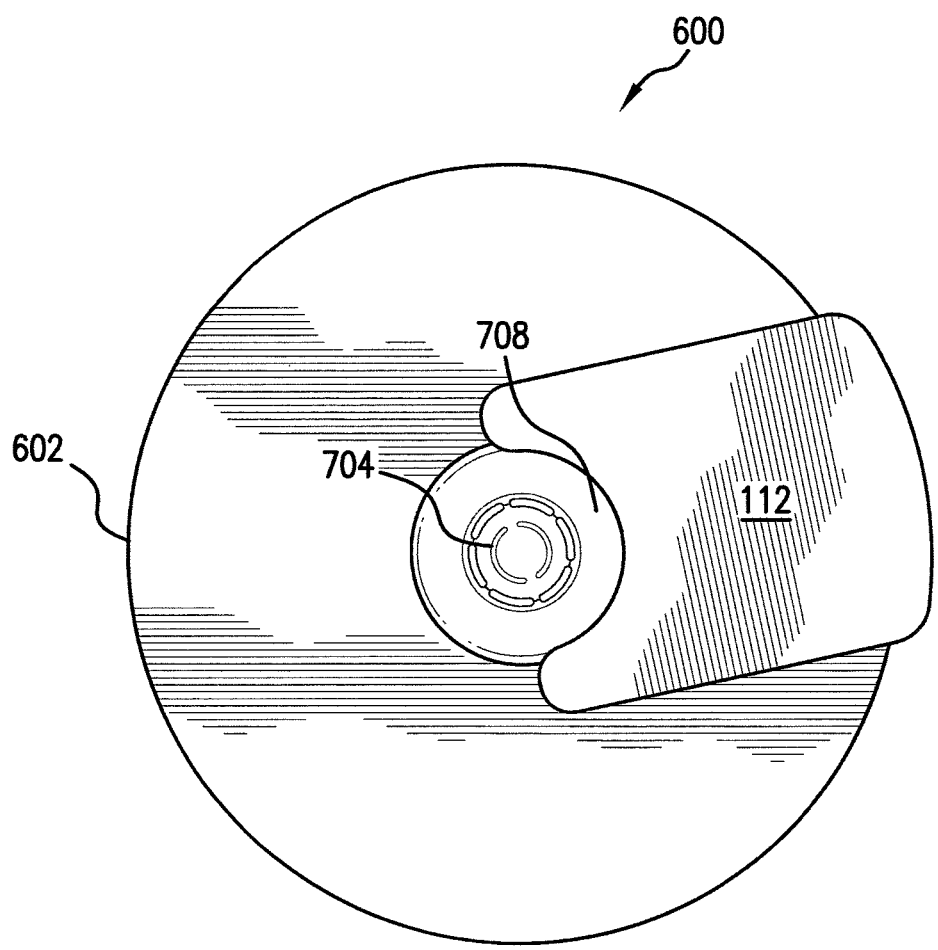
FIG. 7 is a top view of a safety guard in use on a vial of FIG. 6 in an embodiment.

FIG. 7 is a top view of the safety guard 600 of FIG. 6. FIG. 7 illustrates that U-shaped holder 612 covers a portion of disk-shaped shield 602 or the radial opening of disk-shaped shield 602. U-shaped holder 612 has a curved edge 708 to expose the pierce-able cover 704 of vial 606.

It may be desirable for a safety shield to adjust for holding vials of various sizes. In this disclosure, some exemplary designs are presented. In one embodiment, a rotary slider may be included to adjust an opening to fit a vial of any size. In another embodiment, a safety shield may include an Iris capture for adjusting an opening for fitting to a vial of any size.

FIG. 8 is a perspective view of an adjustable safety guard 800 prior to assembly in an embodiment. FIGS. 9A and 9B are perspective views of the adjustable safety guard 800 in assembled condition according to embodiments of the disclosure. The adjustable safety guard 800 includes a rotary slider 802 and a shield base 804. The slider 802 is rotatable against the shield base 804 such that a central opening 818 of the safety guard 800 may be adjusted to fit to a vial neck of any size. The shield base 804 includes a substantially disk-shaped ratchet component 810 and a substantially ring-shaped rail 808. The ratchet component 810 includes a number of railing holding ratchet teeth 838 on its circular outer edge and has a straight inner edge 834 toward central opening 818. The rail 808 extends along the circular outer edge of the ratchet component 810 to guide the rotation of the slider 802. The shield base 804 also includes another curved rail 812, which is on the opposite side of the central opening 818 to the ratchet component 810.

The slider 802 includes a handle 822 for manually rotating the slider against the ratchet component 810. The slider 802 also includes a pawl 814 for locking the slider 802 in a position when one of the teeth 838 is pressed against the pawl 814. This ratchet-pawl mechanism allows the rotation in only one direction, locks the position of the slider 802, and thus fixes the size of the central opening 818 for a particular vial of any size. The slider 802 further includes a slider base component 832 with a slider neck 816 and a curved clearance slot 806 that is aligned with the ratchet component 810 to allow 90 degree articulation of the slider along rails 808 and 812. Specifically, curved clearance slot 806 allows the rotation of the slider 802 under the railing holding ratchet teeth 838. As a result of rotating the slider 802, the central opening 818 is adjusted to fit to a vial of any size.

Safety guard 100 may be made of a plastic. For example, the plastic may be polyethylene or polypropylene. Safety guard 100 may be injection molded and fabricated in one piece. The safety guard may also be fabricated by making U-shaped holder 112 and disk-shaped shield 102 separately, and then assembled them together by using adhesives.

The adjustable safety guard 800 may also be fabricated from plastic like safety guard 100. Additionally, the slider 802, the shield base 804 with ratchet component 810 with rail 808, and rail 812 may be fabricated individually and assembled together to form the adjustable safety guard 800 by a press fit. The handle 822 may be fabricated separately from a slider base component 832 and attached to the slider base component 832 by using an adhesive. The pawl 814 may be fabricated separately from the slider base component 832 and attached to the slider base component 832 by using an adhesive or fabricated with the slider base component 832 together. The fabrication method includes injection molding among others. The ratchet component 810 may be fabricated with a relatively flexible polymer material. The flexible material and curved clearance slot 806 allow the pawl 814 to pass over a tooth when the slider 802 is rotated manually.

In this particular embodiment, the rotation is in a counter clockwise direction as viewed from the top. It will be appreciated by those skilled in the art that the design of the slider, ratchet component, and pawl may vary to allow only clockwise rotation.

FIG. 9A is a perspective top view of the assembled adjustable safety guard of FIG. 8. FIG. 9B is a perspective bottom view of the assembled adjustable safety guard of FIG. 8. FIG. 9C is a top view of slider 802. FIG. 9D is an enlarged view of the ratchet-pawl mechanism with exemplary dimensions in millimeters. The position of the handle 822 is adjustable in a clockwise direction. The spacing between the teeth 838 of the ratchet component 810 and the dimension of the teeth 838 may vary based upon the neck size of the vial. The teeth 838 of the ratchet component 810 may be sloped as illustrated in FIG. 9D. When handle 822 rotates clockwisely, as viewed from the top, outer edge 824 of slider 802 is against curved rail 812, which is slightly concave shaped to guide the rotation of the slider 802. The slider 802 also includes an end portion 826, which is outside rail 808 in assembled condition (see FIG. 9B). The clearance between the outer edge of ratchet component 810 and the inner edge 902 near recessed area allows a press fit for the slider 802 into the shield base 804 during assembling. Note that slider neck 816 has a concaved edge for enclosing a vial neck, as illustrated.

Figure 10A:
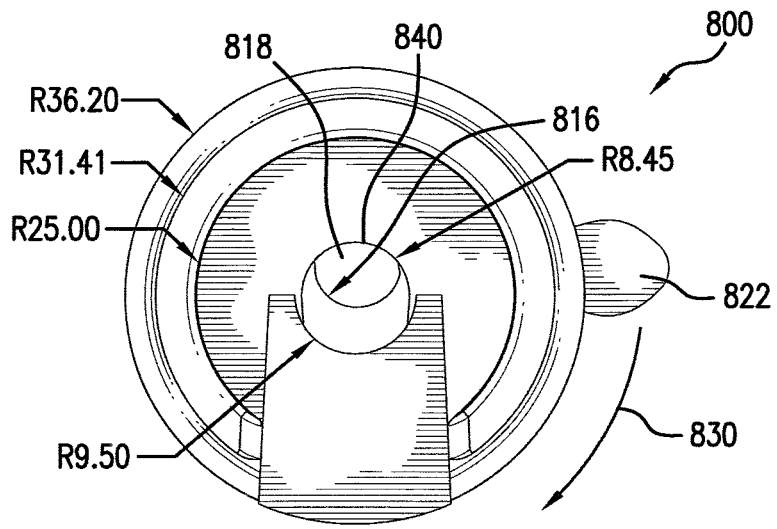
FIG. 10A is a top view of the assembled adjustable safety guard of FIG. 8.
Figure 10B:
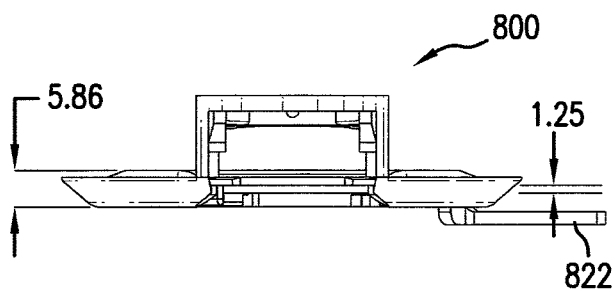
FIG. 10B is a side view of the assembled adjustable safety guard of FIG. 8.
Figure 10C:
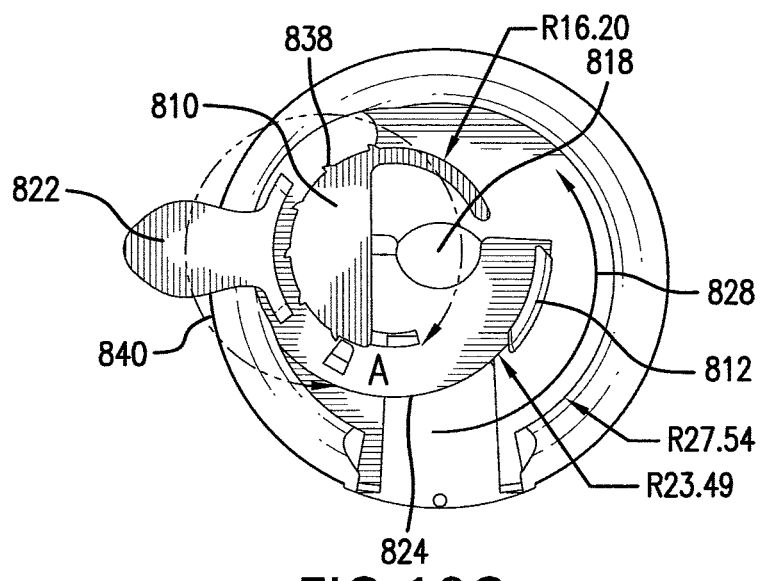
FIG. 10C is a bottom view of the assembled adjustable safety guard of FIG. 8.

FIG. 10A is a top view of the adjustable safety guard 800 in an embodiment. The slider neck 816 and a portion of inner edge 840 of shield base 804 cooperate to form adjustable opening 818 when the handle 822 is turned clockwise as viewed from the top. The adjustable opening 818 becomes smaller when the slider 802 is rotated clockwise, in the general direction of arrow 830. FIG. 10B is a side view of the adjustable safety guard 800 in an embodiment. Note that handle 822 is at the bottom of the adjustable safety guard 800. FIG. 10C is a bottom view of the adjustable safety guard 800 in an embodiment. The handle 822 rotates counter-clockwisely as pointed by arrow 828, as viewed from the bottom. Arrow 840 illustrates the rotation of the slider 802 against the ratchet component 810. Exemplary dimensions in mm are provided as in the FIGS. 10A-10C. It will be appreciated by those skilled in the art that the geometry, shapes, dimensions, configurations of the safety guard or shield may vary. The ratchet-pawl mechanism may also have variations.

Figure 11:
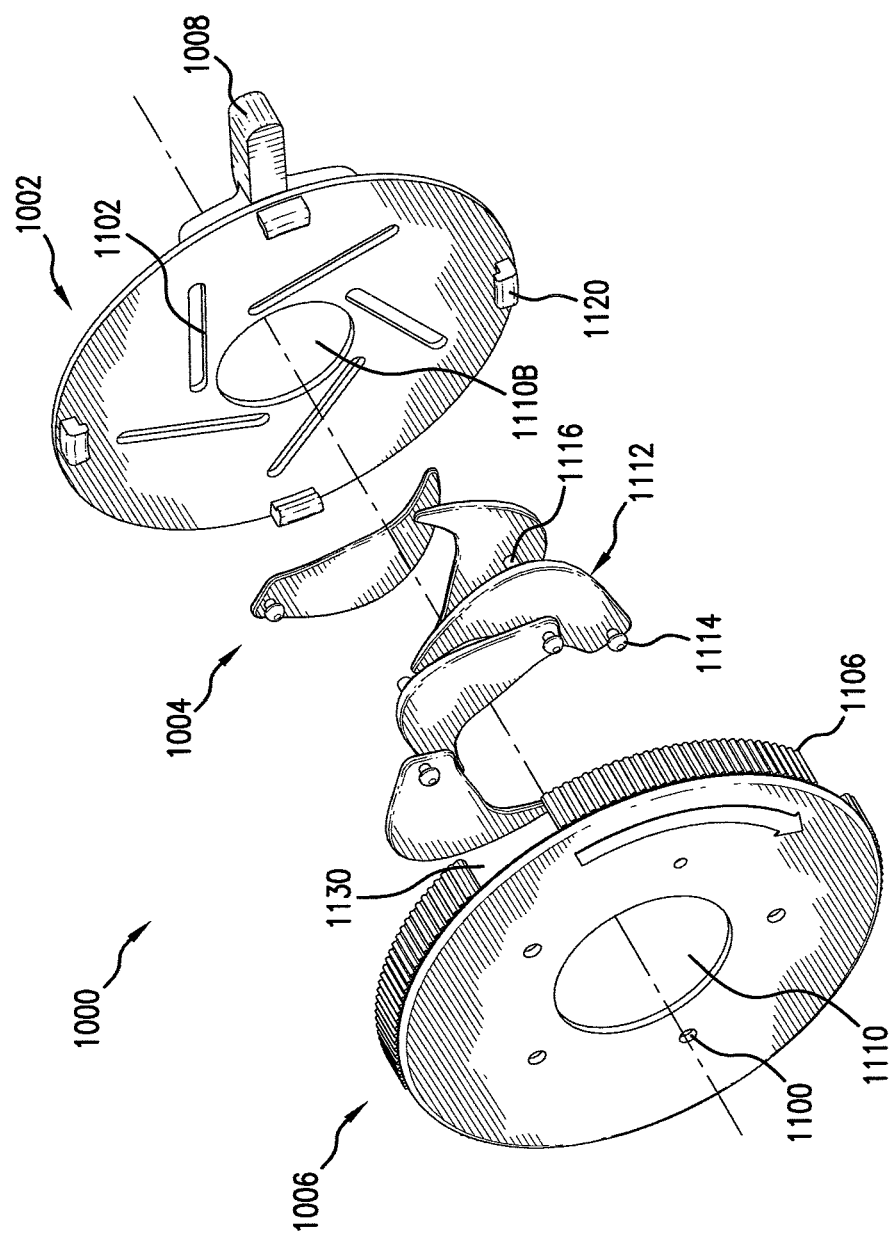
FIG. 11 is a perspective view of a safety shield with an Iris capture for adjustable vial size prior to assembly in an embodiment.

FIG. 11 is a perspective view of a safety shield with an Iris capture for adjustable vial size prior to assembly in an embodiment. Safety shield 1000 includes an upper disk component 1006, an Iris capture component 1004, and a lower disk component 1002. The upper disk component 1006 has an upper central opening 1110A in its center. The upper disk component 1006 also includes a number of blade tabs 1100 arranged circularly around its central opening 1110A. The upper disk component 1006 further includes ribbed sidewalls 1106 extending downward from its outer edge to provide gripping surface for locking position of the Iris capture 1004. The ribbed sidewalls 1106 are spaced by clearance slots 1130 that are areas without any ribbed sidewalls 1106. The Iris capture component 1004 includes a number of Iris capture blades 1112, which are assembled to form the Iris capture. The blade tabs 1100 are used to attach the blades 1112 to the bottom of the upper disk component 1006.

The lower disk component 1002 includes a lower central opening 1110B and a number of linear sliding slots 1102 arranged around the lower central opening 1110B, which is aligned with the central opening 1100 of the upper disk component when assembled. The lower disk component 1002 further includes a handle 1008 attached to its bottom near its outer edge. The lower disk component 1002 also includes a number of snap clips 1120 arranged near its outer edge for attaching to the upper disk component 1006 when assembled. The number of Iris capture blades 1112 is equal to the number of linear sliding slots 1102 and the number of the blade tabs are the same. It will be appreciated by those skilled in the art that the number of Iris capture blades, linear sliding slots, and blade tabs may vary.

Figure 12A:
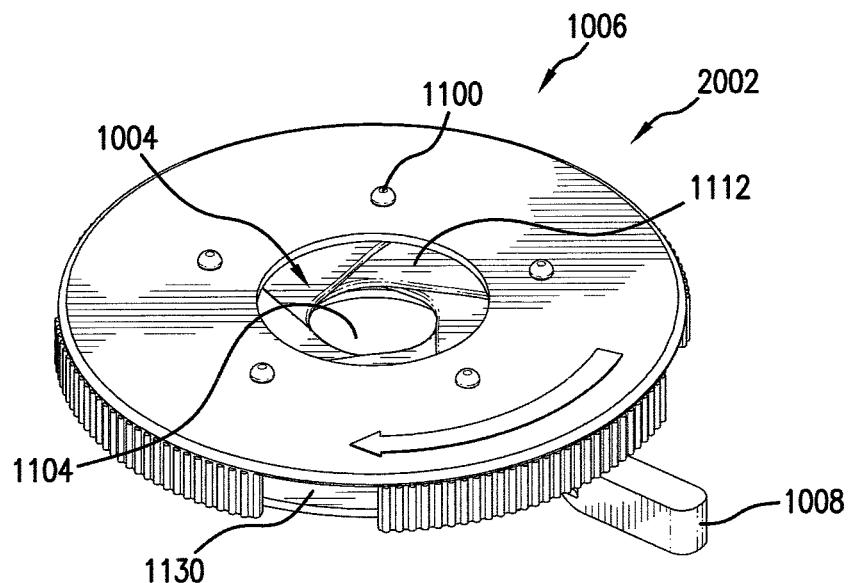
FIG. 12A is a perspective top view of the assembled safety shield with Iris blades of FIG. 11 in an embodiment.
Figure 12B:
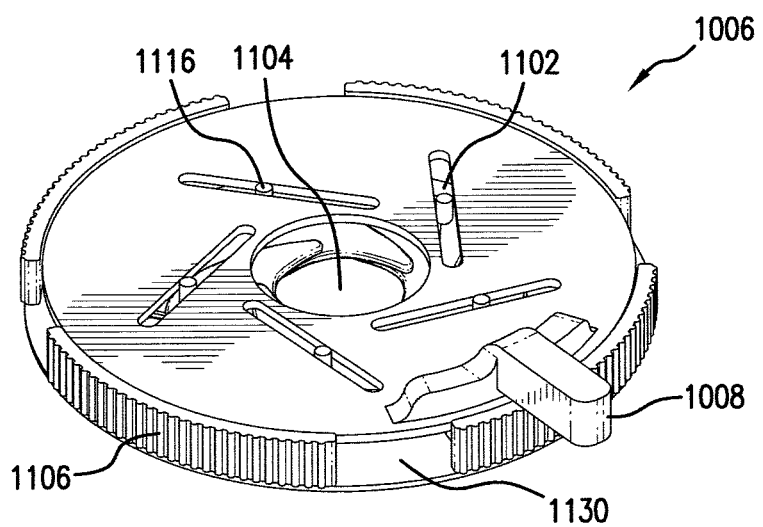
FIG. 12B is a perspective bottom view of the assembled safety shield with Iris blades of FIG. 11 in an embodiment.
Figure 13A:
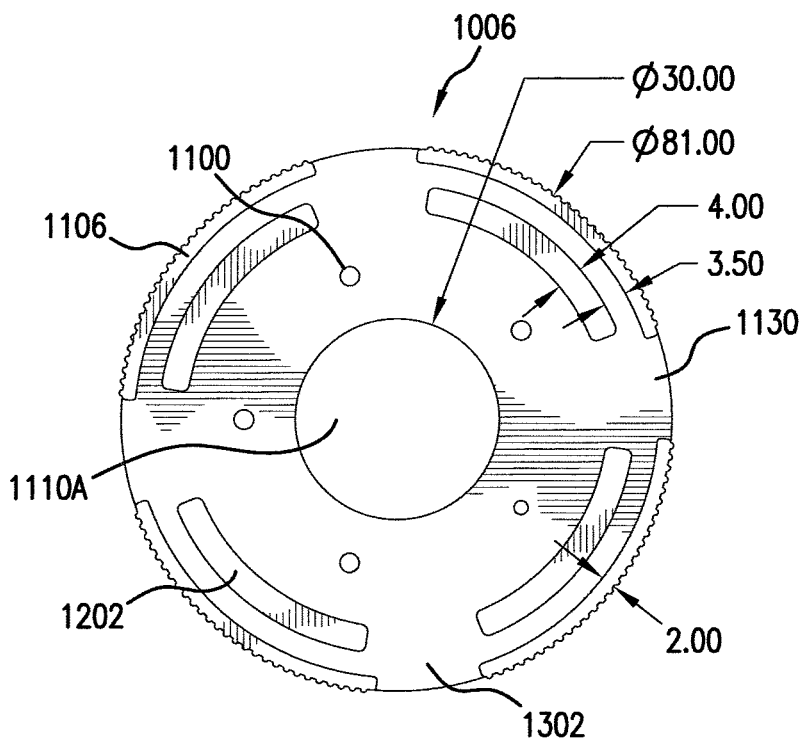
FIG. 13A is a bottom view of the upper disk of the safety shield of FIG. 11.
Figure 13B:
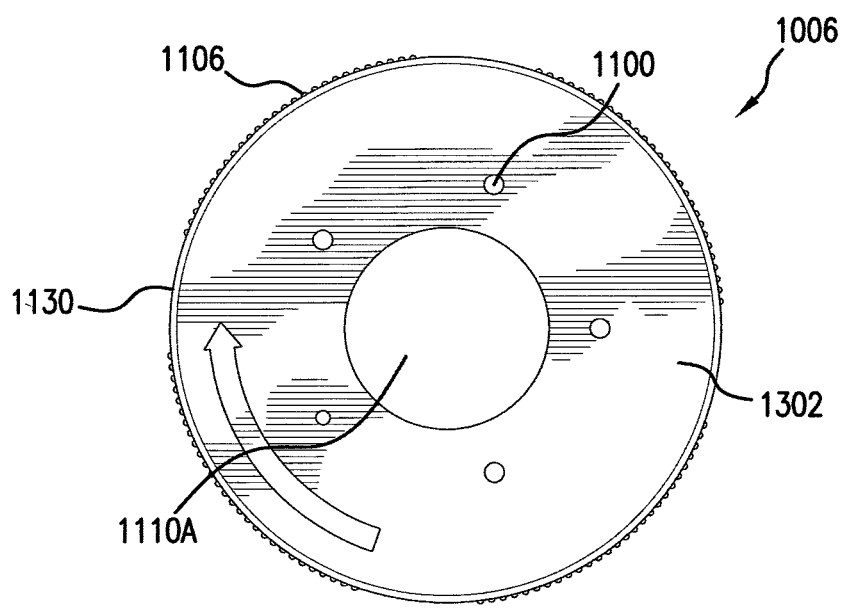
FIG. 13B is a top view of the upper disk of the safety shield of FIG. 11.
Figure 13C:
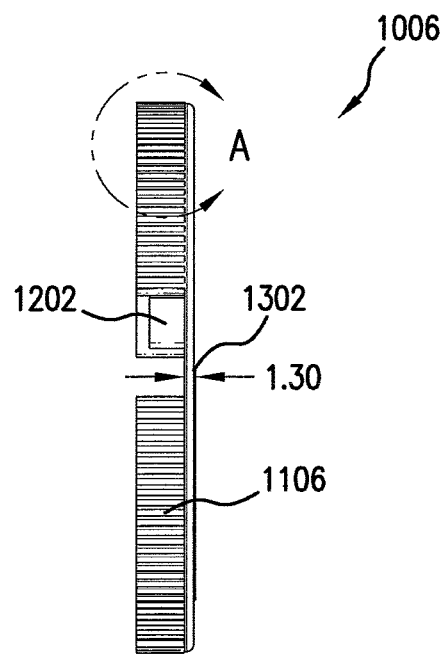
FIG. 13C is a side view of the upper disk of the safety shield of FIG. 11.
Figure 13D:
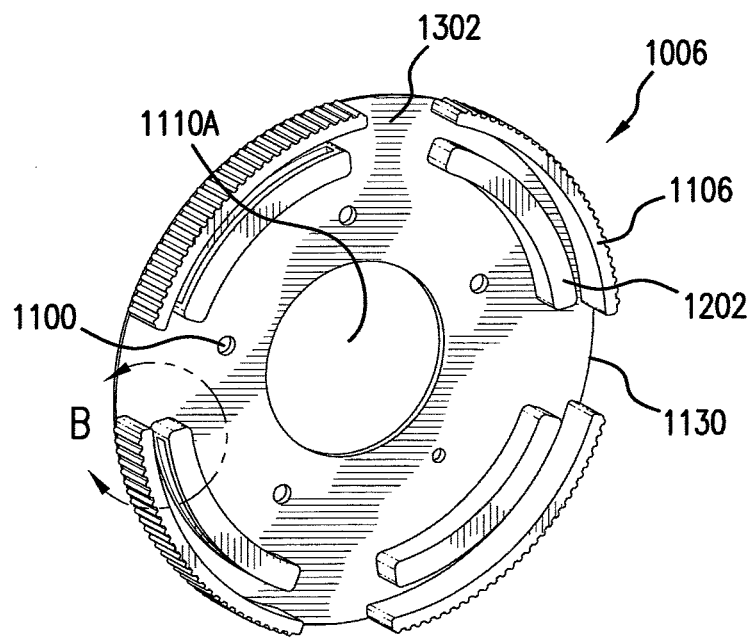
FIG. 13D is a perspective view of the upper disk of the safety shield of FIG. 11.

FIG. 12A is a perspective top view of the assembled safety shield of FIG. 11. FIG. 12B is a perspective bottom view of the assembled safety shield with Iris blades of FIG. 11. When the Iris capture blades 1112 retract and contract with a respective clockwise rotation or counter-clockwise rotation, an Iris opening 1104 enclosed by the blades 1112 is adjusted to fit to the neck size of any vial. The Iris opening 1140 is equal or smaller than both the upper central opening 1110A and lower central opening 1110B. The rotating movements of the Iris blades are enabled by linearly moving the blades 1112 within respective linear sliding slots 1102. Holes 1100 on the upper disk component 1006 are through-holes for the blade tabs 1114 to pass through and to attach the blades to the upper disk component 1006.

FIGS. 13A-D are a bottom view, a top view, a side view and a perspective view of the upper disk component 1006 in an embodiment. The upper disk component 1006 includes a number of snap clip guides 1202 arranged between the holes 1100 and the sidewalls 1106. The snap clip guides 1202 protrude from the disk base 1302 of the upper disk component 1006 for the snap clips 1120 of the lower disk component 1002 to attach the upper disk component 1006 and lower disk component 1002 together. The snap clip guides also provide spacing for the blades 1112 to retract along the respective linear sliding slots 1102 of the lower disk component 1002. The snap clip guides 1202 are curved bars and aligned with the respective ribbed sidewall 1106. The snap clip guides 1202 have heights equal to or less than the ribbed sidewall 1106. The length of the ribbed sidewall 1106 needs to be long enough to cover the entire range of the linear movement of the blade 1112 within the respective slot 1102. The slot size and the configuration of the blades vary with the desirable range of adjustable opening 1104. The upper disk component 1006 also includes clearance slots 1130 between ends of two nearest ribbed sidewalls 1106. The clearance slots 1130 are sized for viewing the snap clips 1120 of the lower disk component 1002 during assembly. Although the exemplary embodiment illustrates four ribbed sidewalls, the number of ribbed sidewalls may vary with the configuration of the blades including the number of blades and arrangement of the blades.

FIGS. 14A-B are a bottom view and a side view of the lower disk component 1002 of the assembled safety shield of FIG. 11. In this particular embodiment, five linear sliding slots 1102 are arranged around central opening 1110B of the lower disk component 1002 for allowing the Iris blades 1112 to rotate. Handle 1008 is located near the outer edge of the lower disk component 1002. When lower disk component 1002 rotates by manually moving handle 1008, snap clips 1120 move along the snap slip guides 1202 and the linear sliding slots move the blades to adjust the Iris opening 1104. Again, the number of sliding slots may vary for other designs. FIG. 14C is a side view of the lower disk snap clip 1120. Note that handle 1008 is on opposite side from snap clips 1120, which are L-shaped.

Figure 15A:
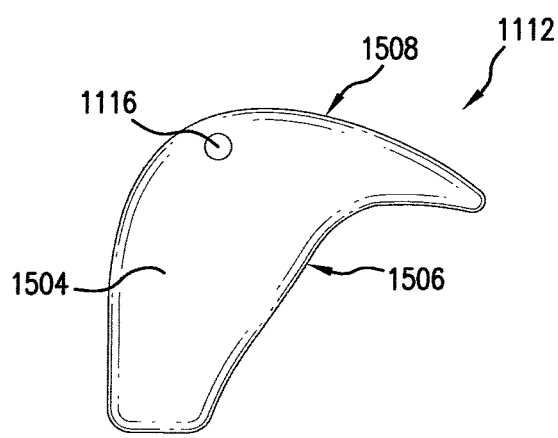
FIG. 15A is a bottom view of the Iris blade of FIG. 11.
Figure 15B:
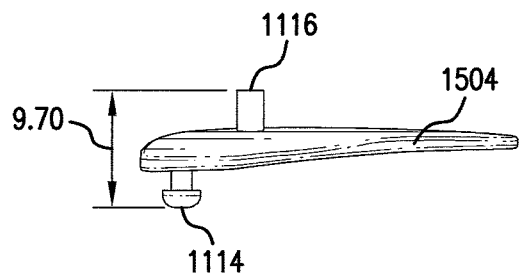
FIG. 15B is a side view of the Iris blade of FIG. 11.

FIGS. 15A-B are a bottom view and a side view of the Iris blade 1112 in an embodiment. Iris blade 1112 includes a blade base 1504, a protrusion 1116 from the blade base on its bottom, which fits to the slot 1102 of the lower shield base 1002. Protrusion 1116 from the blade base 1504 is sized to fit within the slot 1102 to allow the blade to linearly move within the slot 1102. The blade 1112 also includes a clearance hole 1502 on its top side for blade tab 1114 to press fit into. The blade tab 1114 passes through hole 1100 to attach the blades 1112 to the upper disk component. The blade 1112 also includes a curved inner edge 1506 and a curved outer edge 1508 to allow enclosing vials of different sizes.

Exemplary dimensions of the components are provided in millimeters as in the FIGS. 13A-13C, 14A-14C and 15A-15B. It will be appreciated by those skilled in the art that dimensions, shapes, and configurations may vary.

Figure 16:
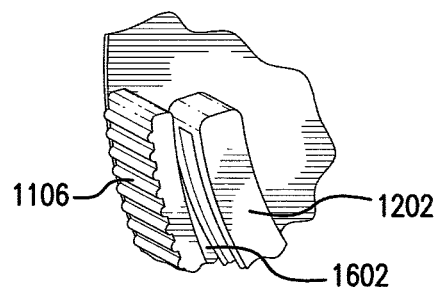
FIG. 16 is an exploded view of the upper disk component near the ribbed sidewall of FIG. 11.

FIG. 16 is an enlarged view of the ribbed sidewall 1106 and the snap clip guide 1202 separated by a clearance 1602. The clearance 1602 is sized to allow the snap slip 1120 to fit in to attach to the snap clip guide 1202. Ribbed sidewall 1106 has a number of grooves to provide gripping surface for a user. When the safety shield 1000 is used, a user may hold the safety shield near the ribbed sidewall with one hand and manually rotates the handle with another hand to adjust the Iris opening 1104 to fit to a vial neck. The safety shield 1000 may also have a locking mechanism (not shown) for locking the Iris opening 1104.

The safety shield 1000 may be fabricated by plastic. For example, the upper disk component, Iris blades and the lower component may be fabricated individually and assembled together to form the safety shield 1000, with the blade tabs and the snap clips. The handle 1008 may be fabricated separately from a disk base 1402 of the lower disk component 1002, and may be attached to the disk base 1402 by using an adhesive (see FIG. 14A). The fabrication method includes injection molding among others.

By using the safety shield 1000, a vial cap may be manually removed, as this safety shield 1000 does not have a cap removal mechanism, like safety guards 100 and 800. The upper disk component 1006 may have a recessed portion (not shown) adapted to collect a needle which may fall onto the safety shield.

One of the benefits of the safety guards 100, 800, and 1000 is to protect a medical assistant from injury. Additional benefit includes that a vial cap may be removed with the U-shape holder in safety guards 100 and 800, rather than manually removing with a hand or other tool. The safety guards 100 and 800 minimize hand contamination on the pierce-able cover of the vial. The vial cap can be removed with the safety guards 100 and 800 without touching the vial cap by a medical personnel. Additional benefit of the adjustable safety guard 800 and safety shield 1000 is to fit to vial necks of various sizes.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed instrumentalities teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A needle safety guard device adapted to attach to a liquid container, the device comprising:
    a shield base having a medial opening connected with a radial opening;
    a ratchet component coupled to a bottom of the shield base;
    a rotary slider coupled to the ratchet component with a plurality of teeth, the slider having a neck portion being movable for fitting to the liquid container;
    a pawl attached to the bottom of the shield base to engage with one of the plurality of teeth of the ratchet component;
    a rail component attached to the bottom of the shield base for retaining the rotary slider; and
    a substantially U-shaped holder coupled to a top of the shield base above the radial opening.

2. The device of claim 1, wherein the neck portion of the rotary slider is substantially concave shaped such that the liquid container partially contacts the neck portion of the rotary slider and partially contacts the medial opening of the shield base and is retained within the shield base.

3. The device of claim 1, wherein the position of the neck portion of the rotary slider relative to the medial opening is adjustable by manually moving a handle coupled to the rotary slider.

4. The device of claim 1, wherein the U-shaped holder comprises two sidewalls coupled substantially perpendicular to the shield base along two radial edges of the radial opening, and a top cover connecting to the two sidewalls and extending from the shield base above the radial opening.

5. The device of claim 1, wherein the U-shaped holder comprises a wedged protrusion and a curved protrusion extending from each of the two sidewalls, the curved protrusion being between the top cover and the wedged protrusion for blocking a cap of the liquid container from moving toward the medial opening.

6. The device of claim 5, wherein the wedged protrusion has a tapered portion near an outer edge of the shield such that the tapered portion generates enough upward wedging force to remove the cap.

7. The device of claim 5, wherein the two sidewalls and the wedged protrusion and the curved protrusion are substantially symmetric to the top cover.

8. The device of claim 1, wherein the shield base comprises a recessed bottom portion below an outer circumferential edge of the disk-shaped shield and an inner circumferential edge around the medial opening.

9. The device of claim 1, wherein the shield base is substantially disk-shaped.

10. The device of claim 1, wherein two radial edges of the radial opening are separated by a distance gradually decreasing toward the medial opening such that the liquid retainer is retained within the medial opening.

11. The device of claim 1, wherein the shield and raised U-shaped holder comprise a plastic.

* * * * *